(12) United States Patent
Thunemann

(10) Patent No.: US 6,395,284 B1
(45) Date of Patent: May 28, 2002

(54) IMMOBILIZATION OF VITAMIN A ACID BY CATIONIC POLYELECTROLYTES

(75) Inventor: Andreas Thunemann, Berlin (DE)

(73) Assignee: Max-Planck-Gesellschaft zur Förderung der Weissenschaften e.V., Munich (DE)

( * ) Notice: Subject to any disclaimer, the term of this patent is extended or adjusted under 35 U.S.C. 154(b) by 0 days.

(21) Appl. No.: 09/492,003

(22) Filed: Jan. 27, 2000

Related U.S. Application Data

(63) Continuation-in-part of application No. PCT/EP98/04644, filed on Jul. 24, 1998.

(30) Foreign Application Priority Data

Jul. 25, 1997 (DE) .......................................... 197 32 139

(51) Int. Cl.⁷ ............................ A61K 9/00; A61K 9/10; A61K 31/20; A61K 47/30; A61K 47/42
(52) U.S. Cl. .................... 424/400; 424/78.02; 514/559; 514/772.3; 514/772.7; 514/773
(58) Field of Search ................................ 424/400, 443, 424/78.02; 514/559, 772.3, 772.7, 773; 562/495; 523/105; 525/50, 54.1, 411, 540

(56) References Cited

U.S. PATENT DOCUMENTS

| 4,371,673 A | * | 2/1983 | Pitha ........................... 525/426 |
| 4,999,348 A | | 3/1991 | Gheorghe et al. ........... 514/182 |

FOREIGN PATENT DOCUMENTS

| DE | 44 28 641 | 2/1996 |
| WO | 96 15810 | 5/1996 |

OTHER PUBLICATIONS

Antonietti et al. Polyelectrolyte–Surfactant Complexes . . . Trends In Polymer Science, vol. 5, No. 8, pp. 262–267, Aug. 1997.*

A. Thunemann, Immobilization of Retinoic Acid by Cationic . . . Langmuir, vol. 13, pp. 6040–6046, Nov. 12, 1997.*

Antonietti et al, "Mesomorphous Polyelectrolyte Surfactant Complexes", Advanced Materials, vol. 7, No. 8, Aug. 1, 1995, pp. 751–753.

Antonietti et al., "Complexation of Lecithin with Cationic Polyelectrolytes: Plastic membranes as Models for the Structure of the Cell membrane", Langmuir, vol. 11, No. 7, 1995, p. 2633–2638.

* cited by examiner

Primary Examiner—Jeffrey E. Russel
(74) Attorney, Agent, or Firm—Arent Fox Kintner Plotkin & Kahn

(57) ABSTRACT

Mesomorphic complexes of vitamin A acid and cationic polyelectrolytes, their preparation and use. The cationic polyelectrolyte, for example PDADMAC, PM4VP, poly(ionene-6,3), polyethyleneimine or a poly-L-amino acid, is mixed with vitamin A acid to produce mesomorphic complexes. Uses of these mesomorphic complexes include the transport of vitamin A in the human body, the treatment of severe cases of acne externally, courses of skin rejuvenation, and the inhibition of malignant tumors.

19 Claims, 14 Drawing Sheets

(1 of 14 Drawing Sheet(s) Filed in Color)

Fig.1
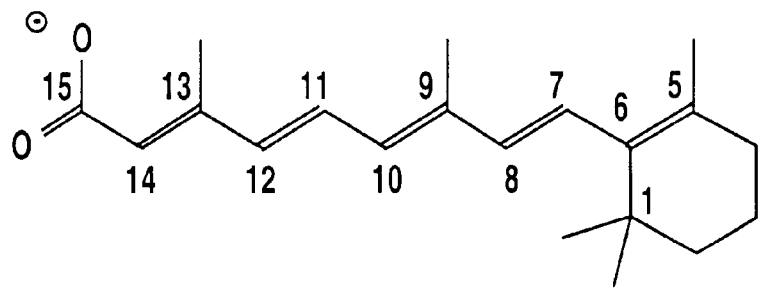
(1)
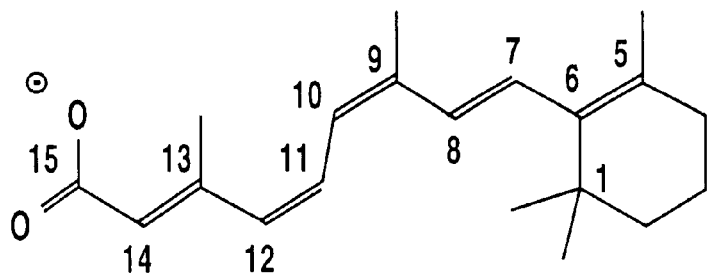
(1')
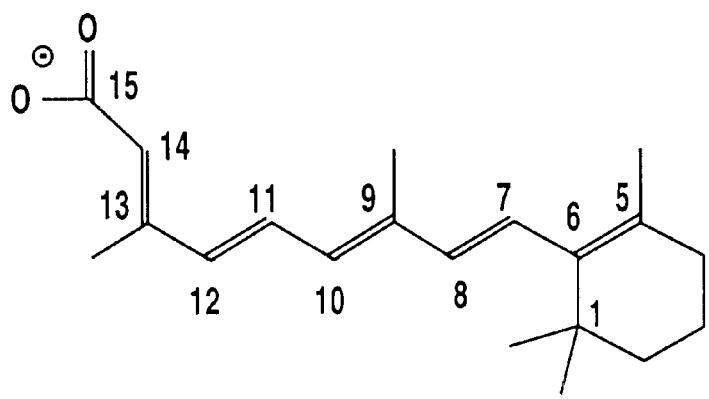
(1")

Fig.2
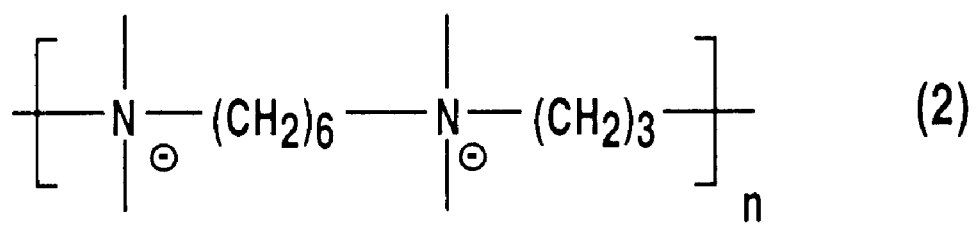
(2)
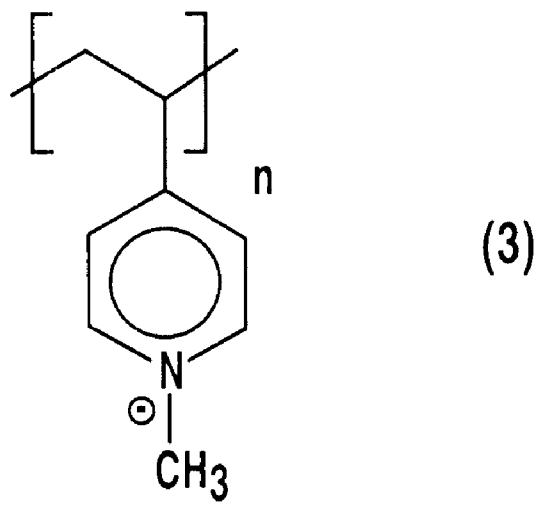
(3)
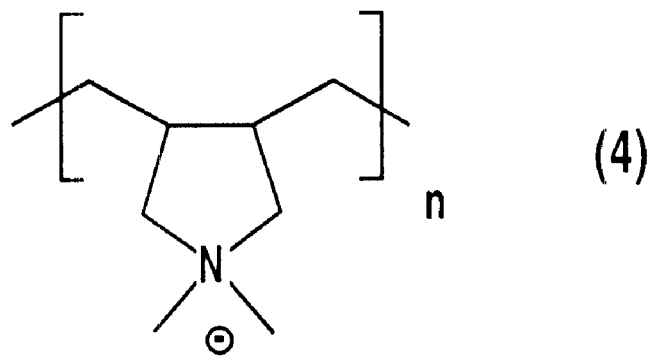
(4)

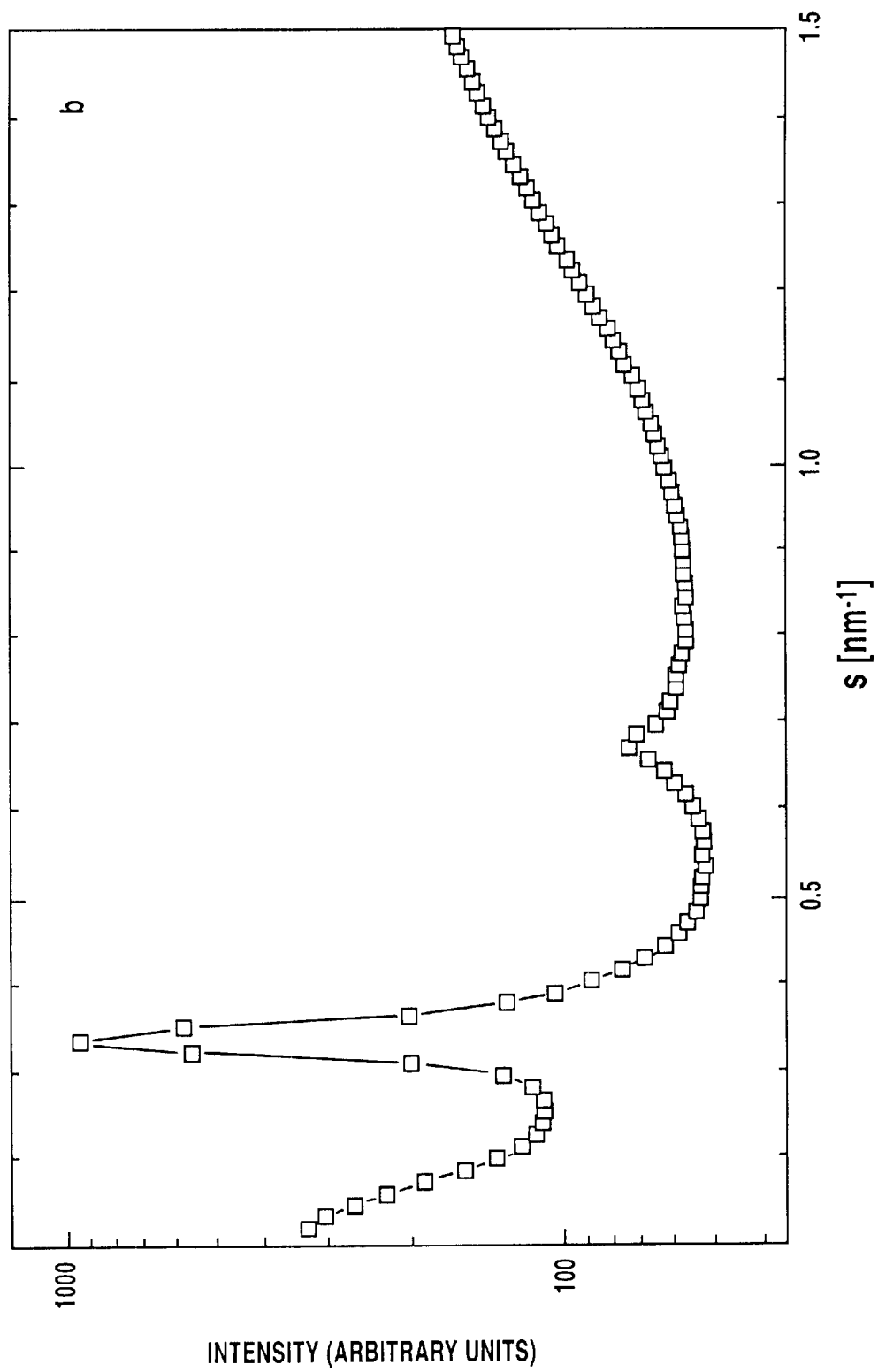

IMMOBILIZATION OF VITAMIN A ACID BY CATIONIC POLYELECTROLYTES

CROSS REFERENCE TO RELATED APPLICATION

This application is a continuation-in-part of International Application PCT/EP98/04644, filed Jul. 24, 1998, and designating the U.S.

The present invention relates to mesomorphic complexes of vitamin A acid and cationic polyelectrolytes, in particular in the form of films or nanodispersions, to process for their preparation and to the use of the mesomorphic complexes as vitamin A substitute.

Vitamin A acid is a highly crystalline low molecular weight material. Lipophilic hormones such as vitamin A acid, steroids, thyroid hormones and vitamin $D_3$ act by binding to ligand-activated transcription factors comprising the steroid/nuclear receptor superfamily (R. M. Evans, Science 240 (1988), 889). Intensive investigations are currently in progress into the role of vitamin A acid in cell differentiation by investigating the binding properties of the retinoids to specific proteins (W. Bourguet, M. Ruff, P. Chambon, H. Gonemeyer and D. Moras, Nature 375 (1995), 377; J. -P. Renaud, N. Rochel, M. Ruff, V. Vivat, P. Chambon, H. Gronemeyer and D. Moras, Nature 378 (1995), 681).

In addition to their important role in the transmission of pleitrophic effects on morphogenesis, differentiation and hemostasis during the embryonic and postnatal phase of life, vitamin A acid shows a great potential as pharmacological active substance. At present, vitamin A acid is used for the external treatment of severe cases of acne, and its use for courses of skin rejuvenation has also been suggested (A. H. Lewin, M. E. Bos, F. C. Zusi, X. Nair, G. Whiting, Bouquin, G. Tetrault and F. I. Carroll, Pharm. Res 11 (1994), 192). Finally, there is also evidence of an inhibition of malignant tumors by retinoids (G. Zanotti, M. R. D'Acunto, G. Malpeli, C. Folli and R. Berni, Eur. J. Biochem. 234(2) (1995), 563; E. P. Jaeger, P. C. Jurs and T. R. Stouch, Eur. J. Med. Chem. 28(4) (1993), 275).

All retinoids have the same characteristic properties as highly UV-active chromophore and have low solubility in aqueous medium and are chemically unstable. This is why, in nature, retinoids bind to specific retinoid-binding proteins which confer protection, solubility and transportability in body fluids. A major problem in relation to the administration of vitamin A acid as pharmacological active substance is the need for immobilization. One possibility of achieving such immobilization and thus a protection of vitamin A acid is to bind it to a protein, as demonstrated in nature. A successful example of this strategy was shown by Zanotti et al., who cocrystallized transthyretin and vitamin A acid. This procedure is, however, difficult and cost-intensive.

European Patent 0 680 748 A1 discloses a composition in the form of a gel which contains an acidic, hydrophilic medium and at least one gel former which is formed from a crosslinked cationic polymer, which is characterized in that the hydrophilic medium is a medium which contains an amount of organic solvent which is 20 to 90% of the total weight of the composition, and contains an amount of water which is not more than 45% of the total weight of the composition, the gel former conferring on the composition a macroscopically homogeneous appearance of a gel and stability, and the cosmetic use of this gel, in particular for skin depigmentation. Gels of this type have an amorphous structure, and their viscosity and thus also their stability is determined by the degree of crosslinking of the polyelectrolytes. The release of a substance present in this gel in unbound form, such as, for example, retinoate, can be controlled by adjusting the viscosity of the gel. The high content of organic solvent in this gel is disadvantageous for use as medicinal product.

It was therefore the object of the present invention to provide a possibility for the immobilization of vitamin A acid which can be carried out easily and with maximal cost-efficiency.

This object is achieved according to the present invention by the provision of mesomorphic complexes of vitamin A acid and cationic polyelectrolytes.

The complexation of vitamin A acid with cationic polyelectrolytes is based on the finding that the formation of ordered structures in solution or in the solid state often takes place by means of self-organization by attachment of a surface-active agent to a polyelectrolyte. The driving force for this process are electrostatic and hydrophobic interactions in aqueous solution. A detailed investigation of self-organized complexes of synthetic polypeptides with surface-active agents having the opposite charge and a low molecular weight has recently been published by E. A. Ponomarenko, A. J. Waddon, D. A. Tirrell and W. J. MacKnight, Langmuir 12 (1996), 2169; A. Ponomarenko, A. J. Waddon, K. N. Bakeev, D. A. Tirrell and W. J. MacKnight, Macromolecules 29 (1996), 4340. It was additionally shown that the complexation of surface-active agents with polyelectrolytes results in a large number of stable mesophases of great structural diversity (M. Antonietti, J. Conrad and A. Thünemann, Macromolecules 27 (1994), 6007; M. Antonietti, S. Henke and A. Thünemann, Advanced Materials 8 (1996), 41; M. Antonietti, A. Kaul and A. Thünemann, Langmuir 11 (1995), 2633). It has also been found that not only synthetic surface-active agents but also amphiphilic compounds might be suitable for this purpose. Vitamin A acid is, on the one hand, polar owing to the presence of the carboxyl functionality and, on the other hand, hydrophobic owing to the presence of the hydrophilic head group and the long hydrocarbon moiety (FIG. 1), that is to say an amphiphilic compound.

Three different polyelectrolytes are preferably used for the complexation of vitamin A acid for the purpose of the present invention. One which has been used is PDADMAC (poly (dimethyldiallylammonium chloride) which is known to form stable soluble complexes with natural lipids (M. Antonietti, A. Kaul and A. Thünemann, Langmuir 11 (1995), 2633; M. Antonietti, A. Wenzel and A. Thünemann, Langmuir 12 (1996), 2111) and forms gels with supramolecular ordering with sodium dodecyl sulfate (F. Yeh, E. L. Sokolov, A. R. Khokhlov and B. Chu, J. Am. Chem. Soc. 118 (1996), 6615). Hence a complex of vitamin A acid with PDADMAC is particularly preferred according to the invention.

Further particularly preferred, structurally different cationic polyelectrolytes which are particularly suitable for complexation for the purpose of the present invention are PM4VP, poly(N-methyl-4-vinyl-pyridine chloride), a polyelectrolyte with charges on the side groups (B. Philipp, W. Dawydoff and K. -J. Linow, Z. Chem. 22 (1982), 1) and poly(ionene-6,3) with the positive charges directly on the main polymer chain (FIG. 2), with PM4VP being referred to as a pendant type polyelectrolyte and poly(ionene-6,3) being called an integral type polyelectrolyte. In respect of its charges, PDADMAC occupies an intermediate position between PM4VP and poly(ionene-6,3). For this reason, PDADMAC is referred to as an intermediate type polyelectrolyte. It is also particularly preferred to use polyethyleneimine, obtainable from BASF, Ludwigshafen, Germany, which is marketed under the Lupasol trademarks.

Further polyelectrolytes which are particularly preferably used are poly-L-amino acids, in particular poly-L-arginine, poly-L-histidine, poly-L-lysine or a mixture thereof. The release behavior of the vitamin A acid present in the complex can be adjusted as required by the choice of the cationic polyelectrolyte.

The ratios of the vitamin A acid and the cationic polyelectrolyte in the complexes according to the invention may vary, with a ratio of 1:1 being particularly preferred. The complexes according to the invention can also easily be processed to film-like structures, so that they are in the form of a visco-elastic film, which have interesting physical properties. In contrast to relatively friable crystalline vitamin A acid, complexes with poly-electrolytes are highly deformable viscoelastic materials. These materials according to the invention show lamellar structures.

In a particularly preferred embodiment, the complexes according to the invention are in the form of particles in a nanodispersion together with a dispersing aid, the particle diameter being ≦5000 nm. All conventional dispersing aids known to the skilled person can be used in this nanodispersion according to the invention, with poloxamer 188 being preferred.

The ratios of the amounts of the complex and of the dispersing aid can be varied in order to obtain a nanodispersion with the properties required in each case, such as, for example, particle size, vitamin A acid release behavior etc. The ratio of complex to dispersing aid is preferably 1:10 to 10:1, particularly preferably 1:2 to 2:1, and it is most preferred for the complex and the dispersing aid to be present in equal amounts in the nanodispersion.

The particle diameter of the nanodispersion is selected appropriate for the requirements for the application. It is preferably 200 to 5000 nm, preferably 250 to 3000 nm, particularly preferably 300 to 2000 nm and most preferably 350 to 1500 nm. In another preferred embodiment the particle diameters are 350 to 400 nm, particularly preferably 350 to 390 nm and most preferably 1350 to 1460 nm. It has surprisingly emerged that the nanodispersion according to the invention is suitable not only for extracorporeal but also for intravenous applications.

The complexes according to the invention and, in particular, PDADMAC retinoate, poly(ionene-6,3) retinoate and PM4VP retinoate are soluble in a large number of polar organic solvents such as methanol, ethanol, 2-butanol, isopropanol and chloroform. Polyelectrolyte complexes with surface-active agents very probably dissociate at least partly in polar solvents (M. Antonietti, S. Förster, M. Zisenis and J. Conrad, Macromolecules 28 (1995), 2270), whereas such complexes may remain associated in solvents of low polarity (K. Bakeev, S. a. Chugunov, I. Teraoka, W. J. MacKnight, A. B. Zezin and V. A. Kabanov, Macromolecules 27 (1994), 3926). The solubility of the preferred complexes according to the invention is consistent with recently published investigations on complexes which consist of conventional synthetic poly-electrolytes and surface-active agents having the opposite charge (M. Antonietti, J. Conrad and A. Thünemann, Macromolecules 27 (1994), 6007).

It has emerged that the complexes according to the invention are suprisingly mechanically stable without crosslinkers, and the stability of the complex according to the invention can be adjusted variably. This means that it is possible in an advantageous manner for the kinetics of release of vitamin A acid from the complex to be controlled in a specific manner and adapted to the particular requirements for application. It has proved to be particularly beneficial that the complexes are mesomorphic with a lamellar structure and, in a particularly preferred embodiment, a physical order state which corresponds to that of a smectic liquid crystal exists.

The complexes according to the invention have advantages in particular by comparison with gels known from the prior art, which are amorphous and for which the chemical behavior of the substances present in them, in particular their release behavior, is determined by the degree of crosslinking, such as, for example, cost-effective production, good storability, simple processibility and usability etc.

In addition, the complexes according to the invention contain only small amounts of or absolutely no organic solvents, so that it has been possible to avoid the use, which is increasingly regarded as critical, of organic solvents, in particular for pharmaceutical applications.

The present invention further relates to a process for the preparation of the complexes according to the invention of vitamin A acid and cationic polyelectrolytes, in which solutions of vitamin A acid and of a polyelectrolyte are mixed, and the crude complexes which have formed are isolated and, where appropriate, purified by methods known per se. In a preferred embodiment of the invention, the polyelectrolyte used is PDADMAC, PM4VP, poly(ionene-6,3), polyethyleneimine or poly-L-amino acids, in particular poly-L-arginine, poly-L-histidine, poly-L-lysine or a mixture thereof. In another preferred embodiment, the process according to the invention is carried out in basic solution, preferably by dissolving vitamin A acid in a basic aqueous solution and then adding an aqueous solution of the polyelectrolyte, preferably dropwise. The complexes according to the invention precipitate during the addition and can easily be removed. For example, further purification can take place by redissolving in methanol, and excess vitamin A acid and salt can be removed by ultrafiltration. The process according to the invention is normally carried out at room temperature, preferably at 20° C. to 30° C., but at not more than 60° C. to 80° C., particularly preferably ≦30° C.

The present invention further relates to the use of the mesomorphic complexes according to the invention, in particular in the form of viscoelastic films or nanodispersions, as vitamin A substitute. It is now possible to use the mesomorphic complexes, which are preferably in the form of viscoelastic films which contain immobilized vitamin A acid, particularly preferably in the form of a nanodispersion, in place of the pure acid for all uses of vitamin A acid for which, in particular, the instability of the acid was disadvantageous.

The complexes according to the invention, in particular in the form of films or nanodispersions, are particularly preferably used as active pharmaceutical ingredients, a suitable and preferred area of application being at present in particular skin disorders or inhibition of the growth of malignant tumors.

The present invention therefore further relates to pharmaceutical compositions which contain the mesomorphic complexes according to the invention, in particular in the form of viscoelastic films or nanodispersions, of the present invention. Pharmaceutical compositions of this type can be employed wherever vitamin A acid or other retinoids have been employed to date.

The complexation of vitamin A acid with cationic polyelectrolytes of various structures (for example integral, intermediate and pendant type) results in the formation of novel materials according to the invention with interesting structural and optical properties as well as novel pharmaceutical compositions. Their main properties are:

1. The novel mesomorphic complexes contain up to 70% by weight optically active molecules. Because of the strong chromophoric interactions in the solid state, the complexes show an additional strong high-energy absorption at 252 nm. In addition, the solid phase Uv/vis spectrum can be significantly influenced by additional chromophores such as, for example, methyl-4-vinylpyridine, which provides further possibilities for altering the absorption characteristics.
2. The complexes can easily be processed to nanodispersions or to films with diverse lamellar structures, which show great morphological similarity to $S_A$ liquid crystals.
3. Depending on the polyelectrolyte structure, the glass transition temperature can be adjusted in the range between −19 and 28° C., and the mechanical properties are also variable within a wide range. From the pharmaceutical viewpoint, the complexes can be regarded as novel formulation of a very active substance. It is to be assumed that the complexes have a reduced toxicity and a reduced teratogenic effect compared with conventional formulations containing vitamin A acid. The complexes can be used to treat skin disorders such as, for example, acne, psoriasis and hyperkeratoses. The formulation of the complexes as colloidal particles might be another way of utilizing the pharmaceutical potential of vitamin A acid for example as active substance for inhibiting the growth of malignant tumors. Vitamin A acid bound ionically to various polyelectrolytes is moreover a promising material for biomimetic applications. It can be assumed that the complexes can also be used as part of a photosynthetic system, in which case protons are transported from the inside of a membrane to the outside, and thus there is formation of an electrochemical gradient which presumably promotes ATP synthesis. In any event, the optical activity of the natural photosensitive pigments is of considerable interest because it allows conclusions to be drawn both about the protein-chromophore interaction and about conformational changes occurring after absorption of light. It is to be assumed that investigation of the uniaxially aligned multilamellar complex films will allow the understanding of the molecular basis of the optical activity of complexes in natural systems to be advanced.

A further embodiment relates to a method for treating a patient with the complexes according to the invention, which are in the form, in particular, of a film or nanodispersion, who is suffering from skin disorders, in particular acne, psoriasis or hyperkeratoses, or from malignant tumors.

The following examples are intended to explain the invention further in conjunction with the figures.
These show This application contains at least one drawing excuted in color.

FIG. 1: the conformations of vitamin A acid: all-trans (1), 11-cis (1') and 13-cis (1")

FIG. 2: polyelectrolytes which are used for the complexation: integral type: poly(ionene-6,3) (2), pendant type: poly(N-methyl-4-vinylpyridinium chloride) (3); intermediate type: poly(diallyldimethylammonium chloride) (4)

Figure 7A:
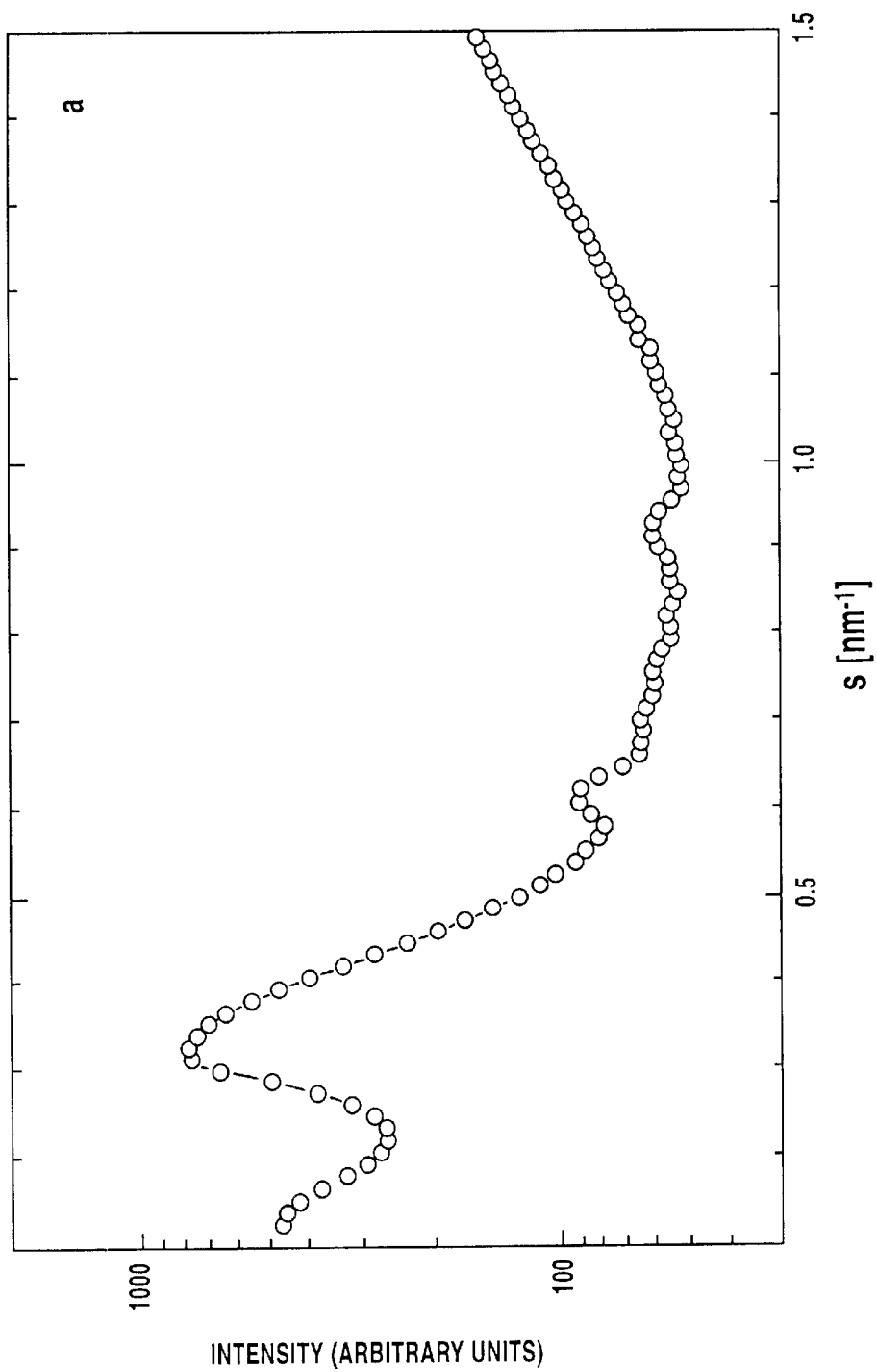
FIG. 7 shows small-angle X-ray scattering diagrams for (a) PM4VP retinoate, (b) poly(ionene-6,3) retinoate and (c) PDADMAC retinoate.
Figure 7C:
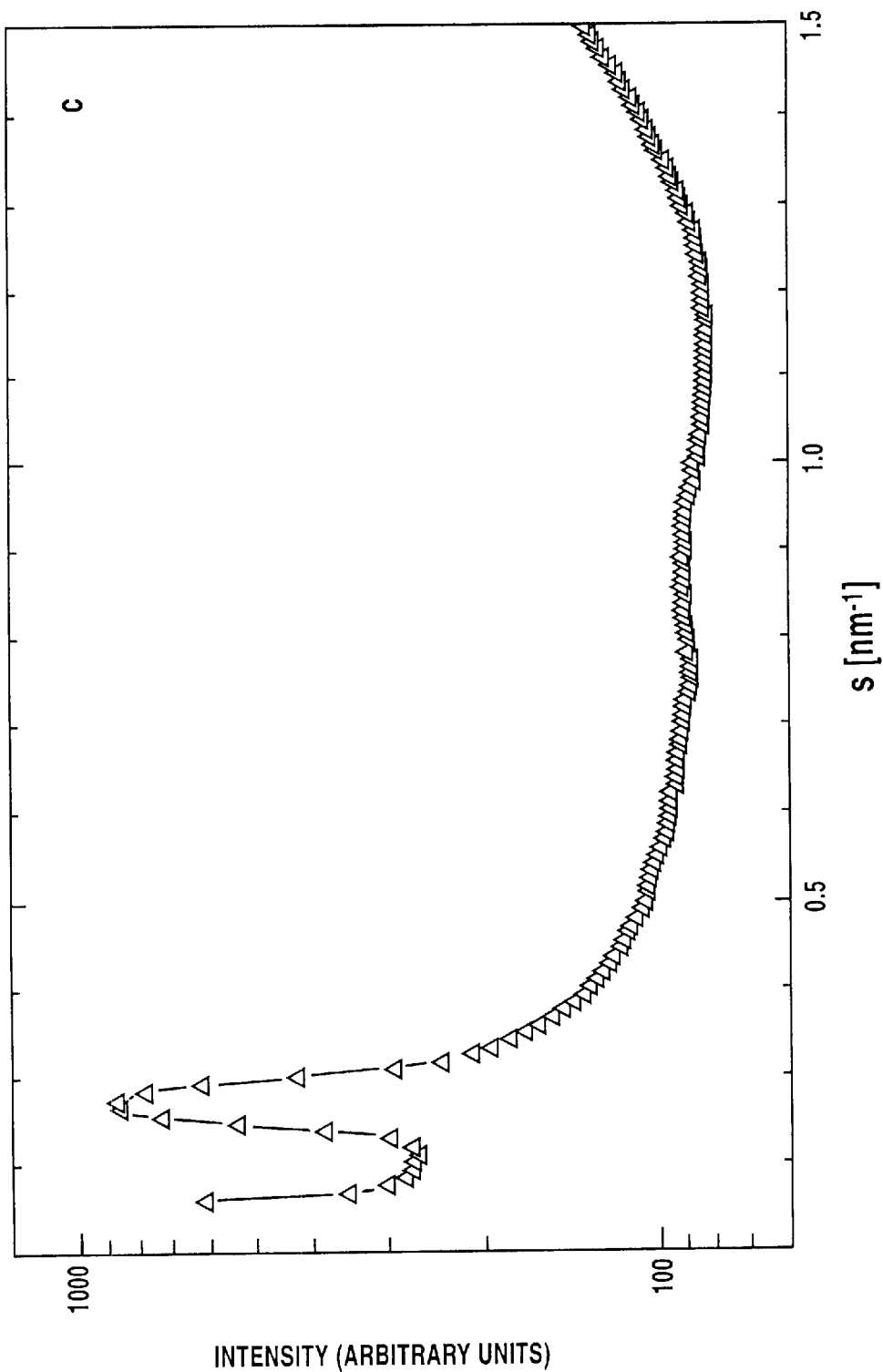

Parts a to c in FIG. 7 show the results of a scattering experiment with small scattering vectors for the three different complexes. Three peaks with spacing ratios of 1:2:3 were found in the diagram for PM4VP retinoate. The diagram for poly(ionene-6,3) retinoate shows two sharp reflections with spacing ratios of 1:2, and that of PDADMAC retinoate has one sharp and two weak, broad reflections with ratios of 1:2:3.

Figure 8C:
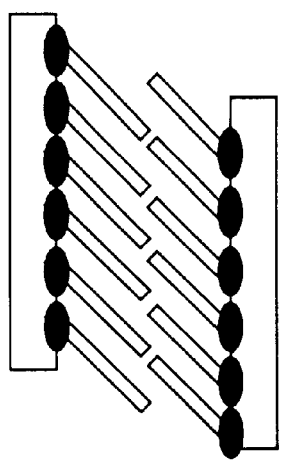
Figure 8B:
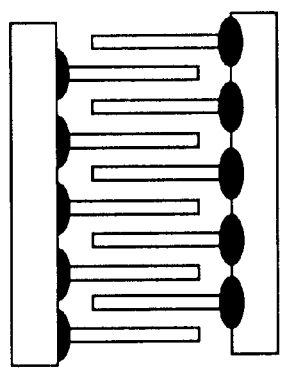
Figure 8A:
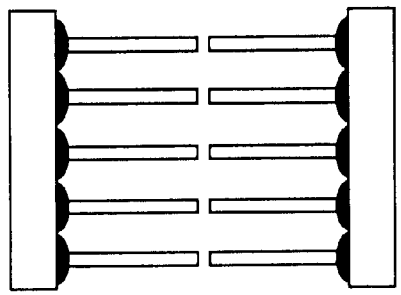

FIG. 8 is a diagrammatic representation of possible structural arrangements of vitamin A-poly-electrolyte complexes. Part a: PDADMAC retinoate; parts b and c: poly(ionene-6,3) retinoate and PM4VP retinoate.

Figure 9:
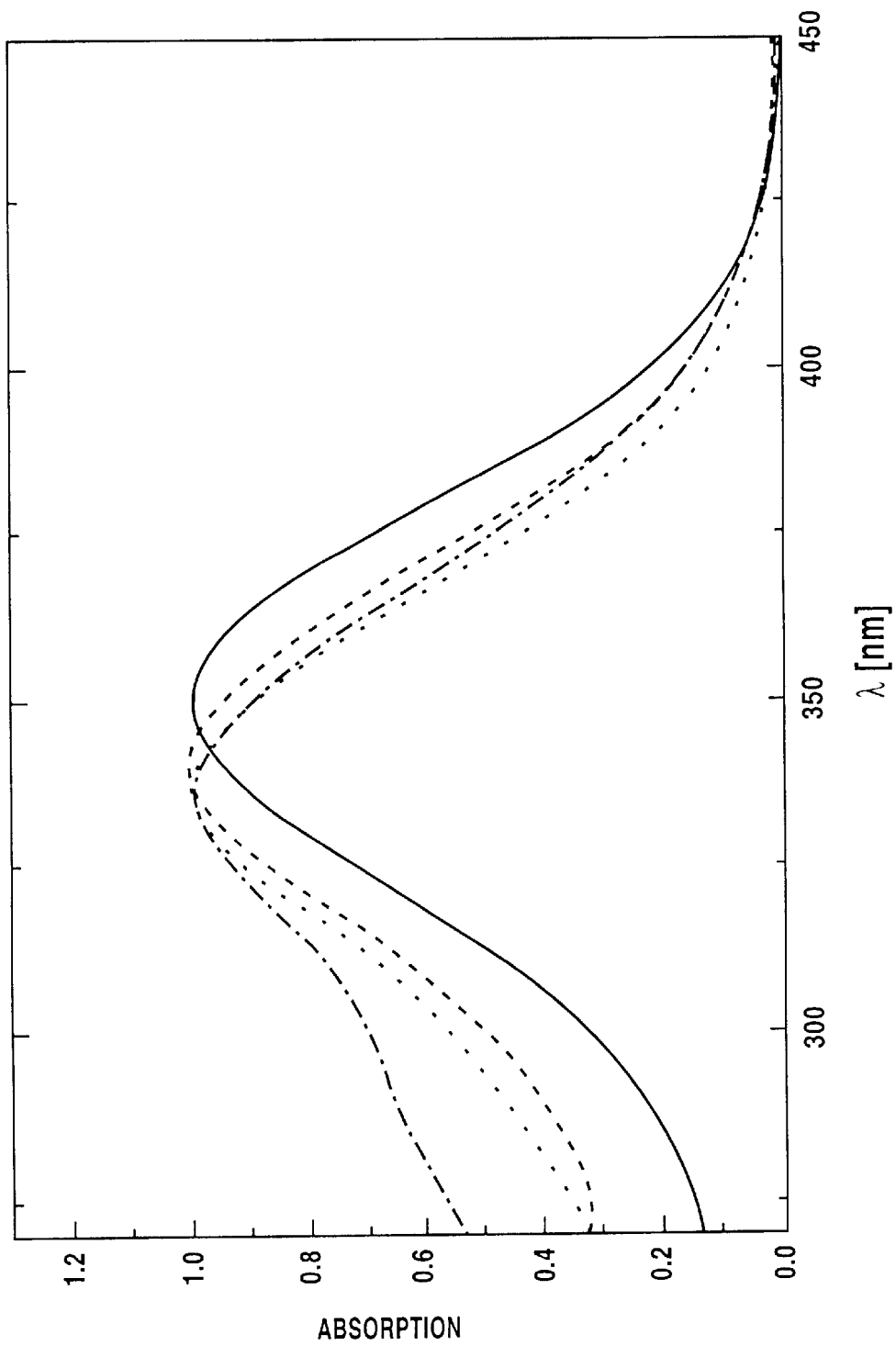

FIG. 9 shows UV/vis spectra of vitamin A acid complexes in methanolic solution: vitamin A acid (full line), PM4VP retinoate (broken line), poly(ionene-6,3) (dotted line) and PDADMAC retinoate (broken/dotted line).

Figure 10A:
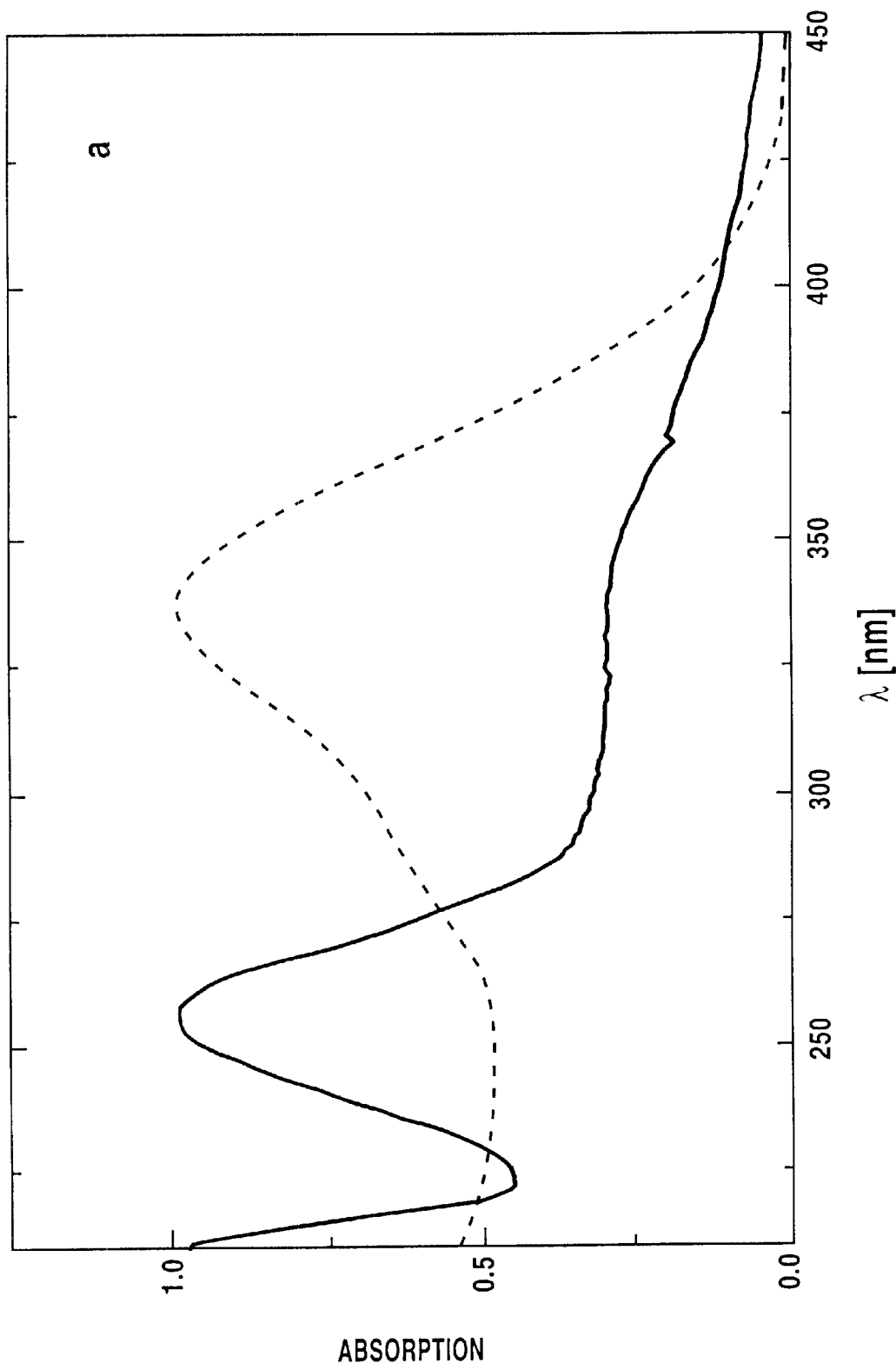
Figure 10B:
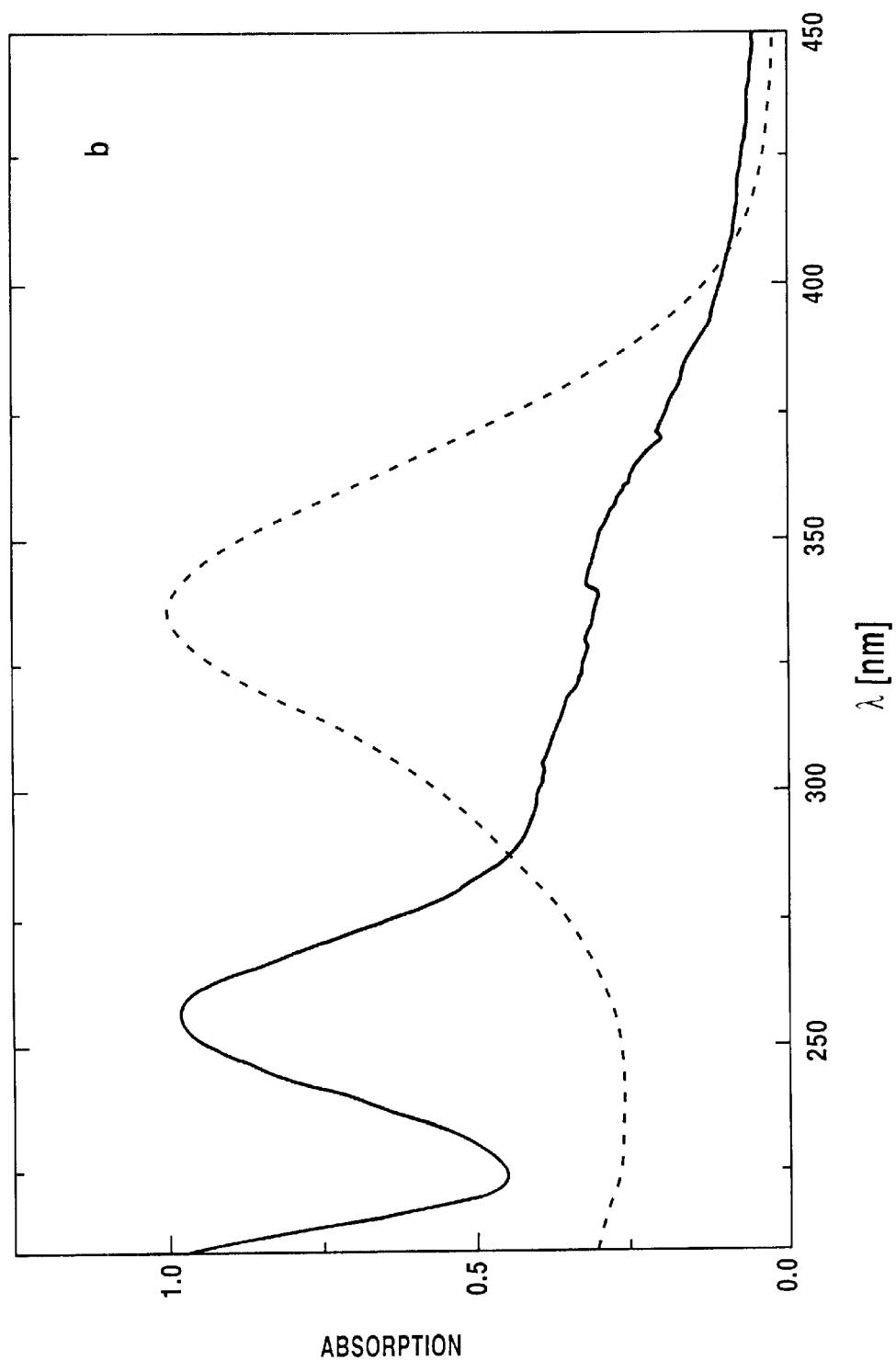

FIG. 10 shows a comparison of the UV spectra of methanolic solution (broken line) and films of vitamin A acid complexes (full line):
PDADMAC retinoate (a), polyionene retinoate (b), PM4VP retinoate (c).

EXAMPLE 1

Materials

Crystalline all-trans vitamin A acid (tretinoin) as powder, high molecular weight poly(diallyldimethyl-ammonium chloride) (20 w/w aqueous solution) and high molecular weight poly(ionene-6,3 bromide) were purchased from Aldrich Chemical Co. The molecular weight of poly (diallyldimethylammonium chloride) was found to be $M_w$=180,000 g/mol by viscosimetry in 0.5 N sodium chloride salt solution. The result of an aqueous GPC was $M_w$=623,000 g/mol, $M_n$=187,000 g/mol, and light scattering gave a value of 525,000 g/mol. The very different values indicate the general problem of accurate molecular weight determination for poly-electrolytes. However, wide molecular weight distribution and the inaccuracy of the molecular weight determination is of no further relevance to the complex formation. Poly(N-methyl-4-vinylpyridinium chloride) was prepared by reaction of poly(4-vinylpyridine) with three equivalents of methyl iodide in nitromethane. Iodide was replaced by chloride by ultrafiltration using a sodium chloride solution. The yield from the methylation was determined by $^1$H-NMR spectroscopy to be 100%. The poly(4-vinylpyridine chloride) was prepared by a free-radical polymerization reaction in solution (R. M. Fouss, M. Wanatabe and B. D. Coleman, J. Polym. Sci. 48 (1960), 5). Its molecular weight was determined by THF-GPC to be $M_w$=180,000 g/mol. The high molecular weight stated for poly(ionene-6,3 chloride) by the supplier is somewhat misleading because no molecular weights higher than 30,000 to 50,000 g/mol are in fact available. The molecular weight of the poly(ionene-6,3 chloride), which was used in the present examples, was found by light scattering to be of the order of 5000 g/mol. The solvent for producing the films was HPLC-purified methanol (HPLC grade methanol (Aldrich Chemical Co.)).

1.1 Complex formation 100 mg of vitamin A acid were dissolved in aqueous sodium hydroxide solution, and a 0.5% strength aqueous solution of the polyelectrolytes was added dropwise while stirring until no further precipitation was observed. The resulting crude complexes were removed and redissolved in methanol. Excess vitamin A acid and salt were removed by ultrafiltration. Elemental analysis of all the complexes showed that less than 0.01% of sodium and chloride (or sodium and bromide) was present. Free-standing films of all three complexes were cast by pouring their solutions in methanol or ethanol onto glass plates. The two-dimensional geometry of the films was determined by glass frames of various size which were fixed to the glass plate. After evaporation of the solvent at 20° C., traces of the solvent remained and were removed in vacuo at room temperature over 24 hours.

1.2 Methods

Wide-angle X-ray scattering investigations (WAXS) were carried out with a Nonius PDS120 powder diffractometer in transmission geometry. An FR590 generator was used as source of Cu-Kα radiation, the primary ray was made monochromatic by a curved Ge crystal, and the scattered radiation was measured using a CPS120 position-sensitive detector. The resolution of this detector is better than 0.018°. X-ray small-angle scattering curves (SAXS) were recorded with a vacuum X-ray camera with pinhole collimation (Anton Paar, Austria, model A-8054) which was equipped with image plates (type BAS III, Fuji, Japan). The image plates were read using a MACScience IRP-420 dip-scanner and DIPR-420 PI reader (Japan). DSC measurements were carried out in a Netzsch DSC 200 (Germany). The samples were investigated with a heating rate of 10 K/min in two heating and two cooling cycles. The first and second cycles were essentially identical. Stress-strain investigations were carried out with a Zwick material tester with the number Z010 (Germany). Optical microscopic investigations with polarized light on the film were carried out, with a Zeiss DMRB microscope (Germany). The TV/vis spectra were recorded in a UVICON 931 spectrophotometer from Kontron Instruments. Simulations of molecular arrangements of the complexes were carried out using Insight & Discover (BIOSYM Technologies, USA).

EXAMPLE 2

Stress-strain Investigations

Figure 3:
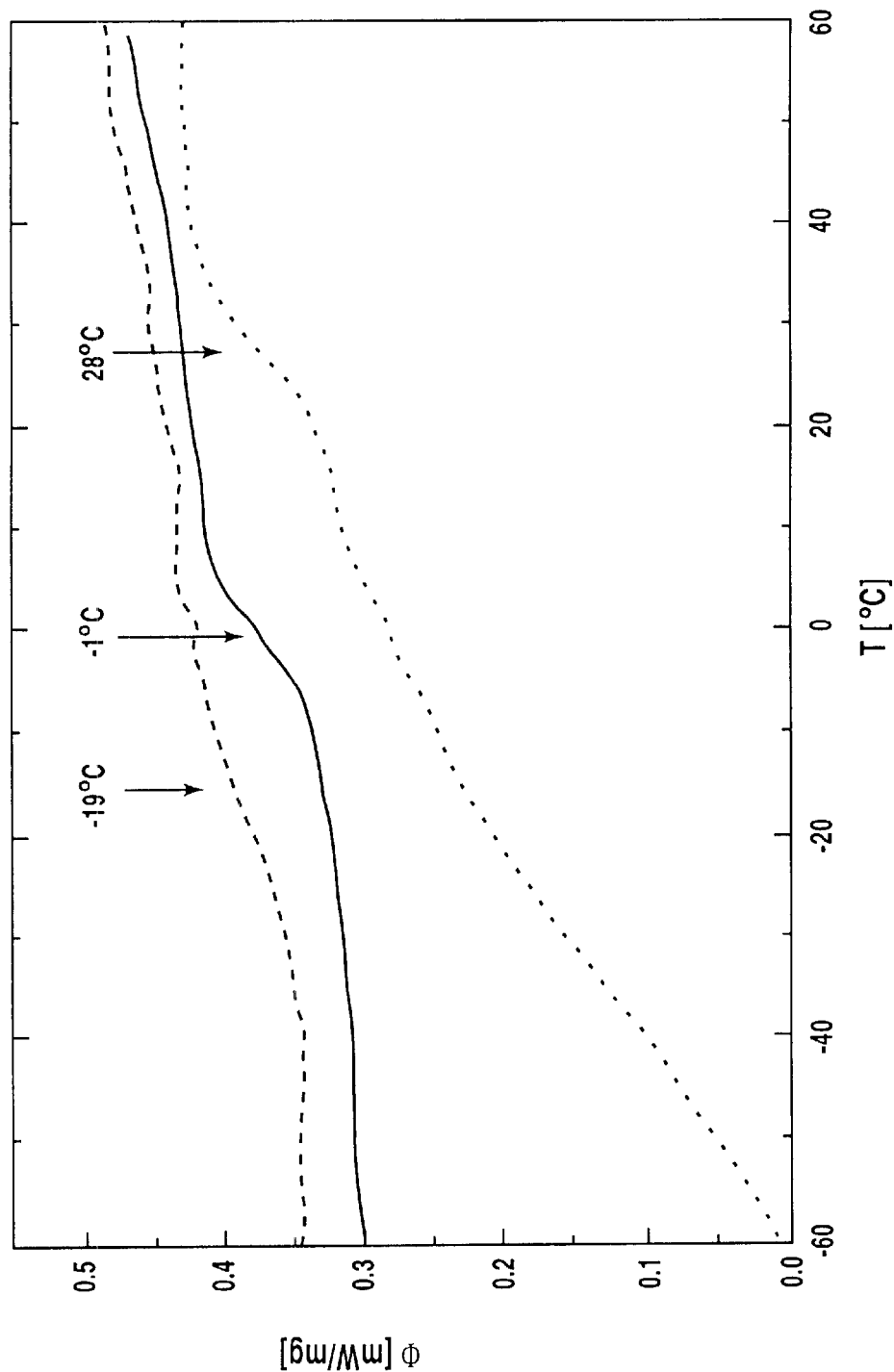
FIG. 3 shows DSC curves of PM4VP retinoate (broken line), poly(ionene-6,3) retinoate (full line) and PDADMAC retinoate (dotted line).
Figure 4:
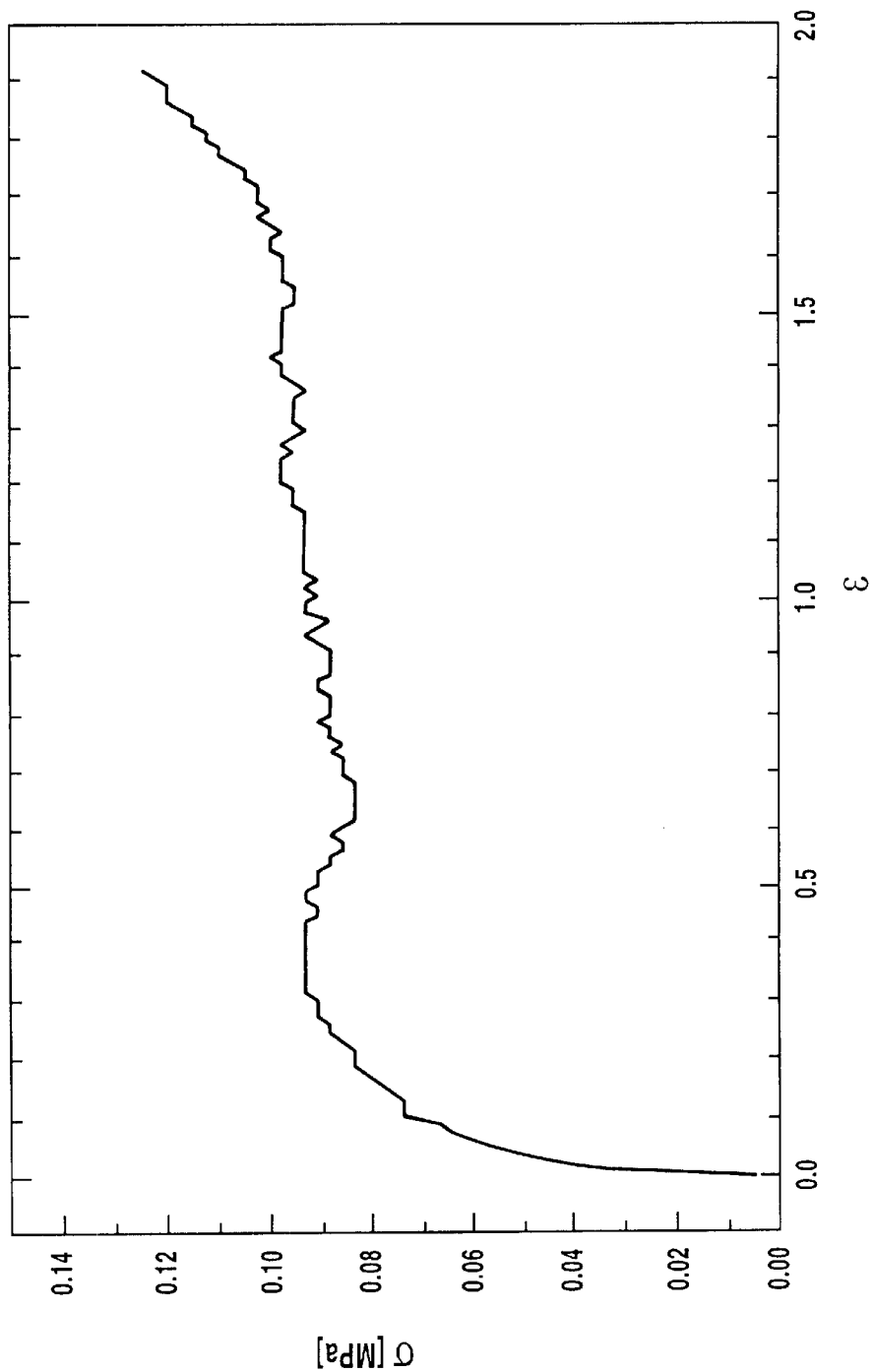
FIG. 4 shows a stress-strain diagram for PDADMAC retinoate in the form of a film.

Because of the high glass transition temperature, films cast from PDADMAC retinoate are the most mechanically stable in the series. It was therefore possible to carry out stress-strain experiments. A typical stress-strain curve for a PDADMAC retinoate film is shown in FIG. 4. The stress-strain behavior is similar to that typically observed for rubber-like material. The tensile strength modulus of PDADMAC retinoate at an elongation of 1% was determined to be 4 MPa. Elongation at constant tensile stress was observed in the range between 30 and 150%. During further elongation, the stress rises to a maximum of 0.125 MPa. The material tears at an elongation of 200%. It is remarkable that such a flexible film, consisting mainly of rigid, rod-like molecules, is formed. Responsible for this are interactions at the molecular level and, in particular, Coulomb forces between retinoate units and the polyelectrolytes, with conversion of friable crystals into viscoelastic polymers.

EXAMPLE 3

Optical Microscopy

Figure 5:
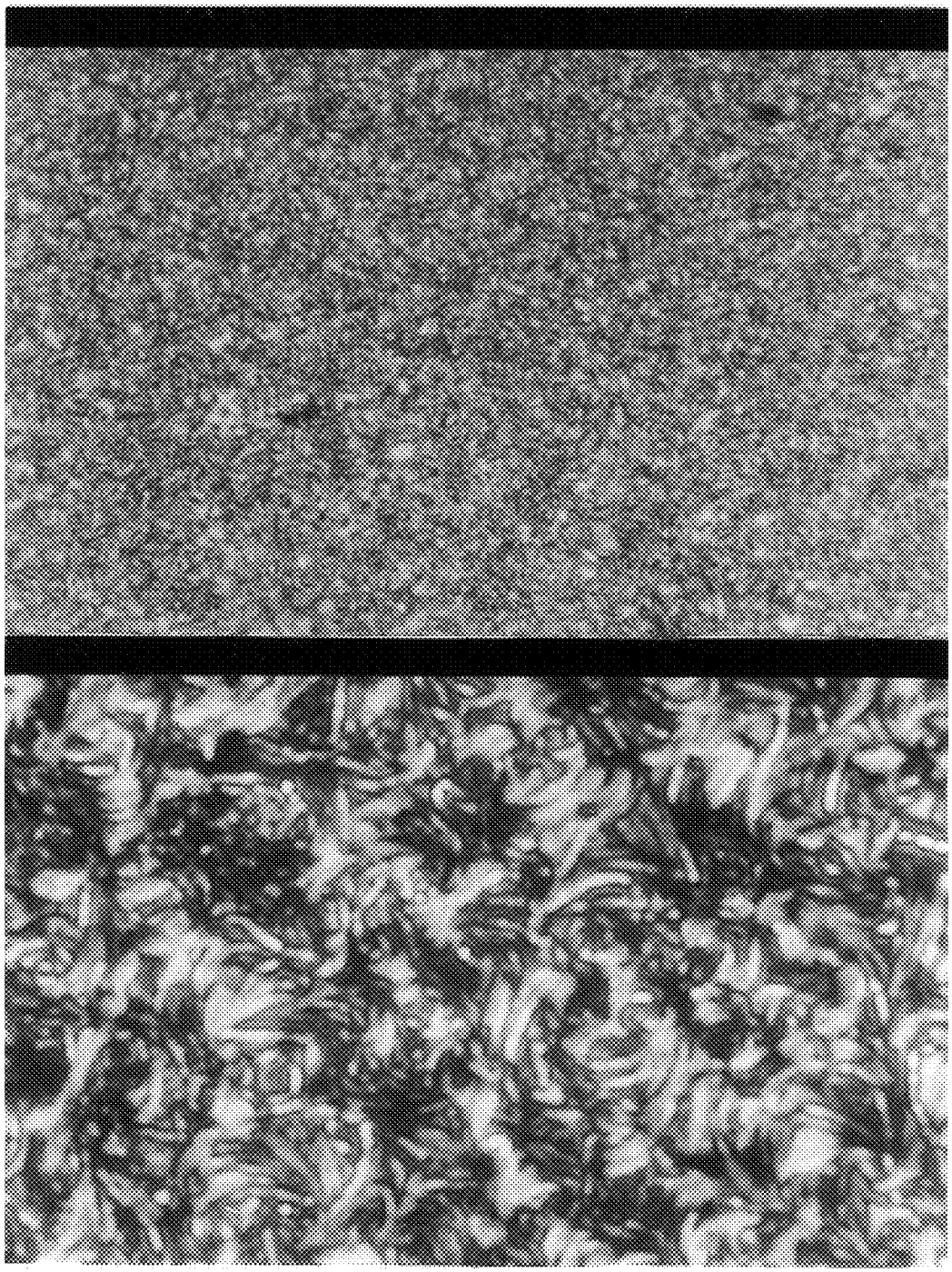
FIG. 5 shows a polarization micrograph of a PDADMAC retinoate film.

The films of all the complexes are optically anisotropic, as was found during an investigation between crossed polarizers. One example of the optical texture is shown in FIG. 5. The complexes are evidently mesomorphic materials, but unambiguous identification of the mesophase is not possible on the basis of the optical texture.

EXAMPLE 4

X-ray Scattering

Figure 6:
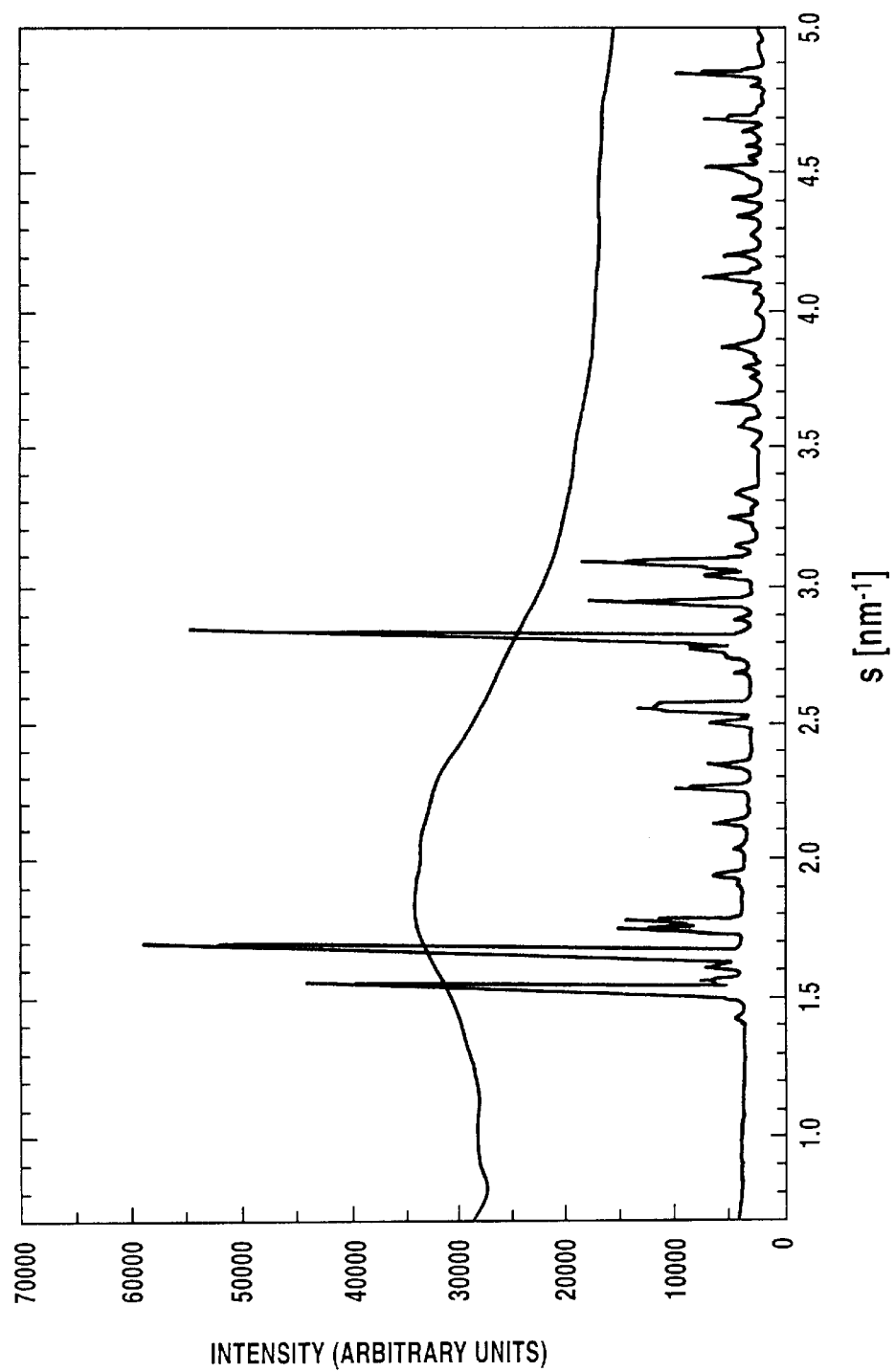
FIG. 6 shows wide-angle X-ray scattering from a PDADMAC retinoate film (upper curve) and retinoate powder (lower curve).

The absence of sharp reflections in the wide-angle apparatus proves that the three preferred retinoate complexes are in fact amorphous. The diagrams for the three complexes are essentially identical. As an example, the WAXS curve for PDADMAC is shown in FIG. 6. The scattering curve shows a characteristic amorphous halo corresponding to a Bragg distance of about 0.52 nm. This figure is considerably larger than that observed for an amorphous packing of saturated alkyl chains in complexes of surface-active agents with low molecular weight with synthetic polypeptides (0.45 nm) (A. Ponomarenko, A. J. Waddon, K. N. Bakeev, D. A. Tirrell and W. J. MacKnight, Macromolecules 29 (1996), 4340) or that observed for polystyrenesulfonate surface-active agent complexes (0.43 nm) (M. Antonietti, J. Conrad and A. Thuenemann, Macromolecules 27 (1994), 6007). The lower maximum position of the amorphous halo in the retinoate complex compared with that observed in complexes with saturated alkyl chains indicates that the average atomic distance is considerably larger in the aforementioned. This is to be expected on the basis of the protruding hexene ring and the alkylene unit, conjugated therewith, of the retinoate, for which reason the molecules cannot pack together amorphously with the same density as flexible chains. Free vitamin A acid has a great tendency to crystallize (FIG. 6) and two similar crystalline modifications of vitamin A acid are known (a triclinic and a monoclinic) (C. H. Stam, Acta Cryst. B28 (1972), 2936). As shown in FIG. 6, the ability of vitamin A acid to crystallize is greatly diminished by the complexation with a polyelectrolyte. The complexes remain amorphous for several months, and it can be concluded from this that they are thermodynamically stable.

Parts a to c in FIG. 7 show the results of a scattering experiment with small scattering vectors for the three different complexes. Three peaks with spacing ratios of 1:2:3 were found in the diagram for PM4VP retinoate. The diagram for poly(ionene-6,3) retinoate shows two sharp reflections with spacing ratios of 1:2, and that of PDADMAC retinoate has one sharp and two weak, broad reflections with ratios of 1:2:3.

EXAMPLE 5

UV/vis Spectroscopy

The great effect of the complexation on the optical properties can best be shown by comparing the UV/vis absorption spectra of the complexes in a film in methanolic solution (Table 1). The UV/vis spectrum of the pure all-trans vitamin A acid in methanol shows only one broad peak with a maximum at 348 nm. The spectra of redissolved complex films are very similar to that of pure all-trans vitamin A acid. Only a small hypsochromic shift in the range from $\Delta\lambda_{max}=8$ nm (PM4VP retinoate) to 12 nm (PDADMAC retinoate) was found (FIG. 9). It was concluded from this that no significant chromophore interaction takes place in the solution, and the retinoate units behave like isolated chromophores. On the assumption that the hypsochromic shift serves as a qualitative measure of the binding constant, the following series was obtained for increasing binding strength: PM4VP retinoate<poly(ionene-6,3) retinoate<PDADMAC retinoate. This sequence is consistent with the DSC results in which increasing glass transitions were found in the same sequence.

The absorption behavior of the complexes in films is different from that in solution (FIG. 10a–c) : The spectrum of solid PDADMAC retinoate shows an additional absorption maximum at 252 nm, which is stronger than the second at 319 nm. Compared with the solution, an additional hypsochromic shift of $\Delta\lambda_{max}$=17 nm is observed for the latter in a film. A very similar spectrum to that for PDADMAC retinoate was found for poly(ionene-6,3) retinoate films (FIG. 10b): The absorption maximum at 253 nm is characteristic in this case. Once again, the maximum is considerably stronger than the second absorption band at 297 nm. This once again shows an additional hypsochromic shift of $\Delta\lambda$.max=40 nm compared with the UV/vis of the complex in solution.

Figure 10C:
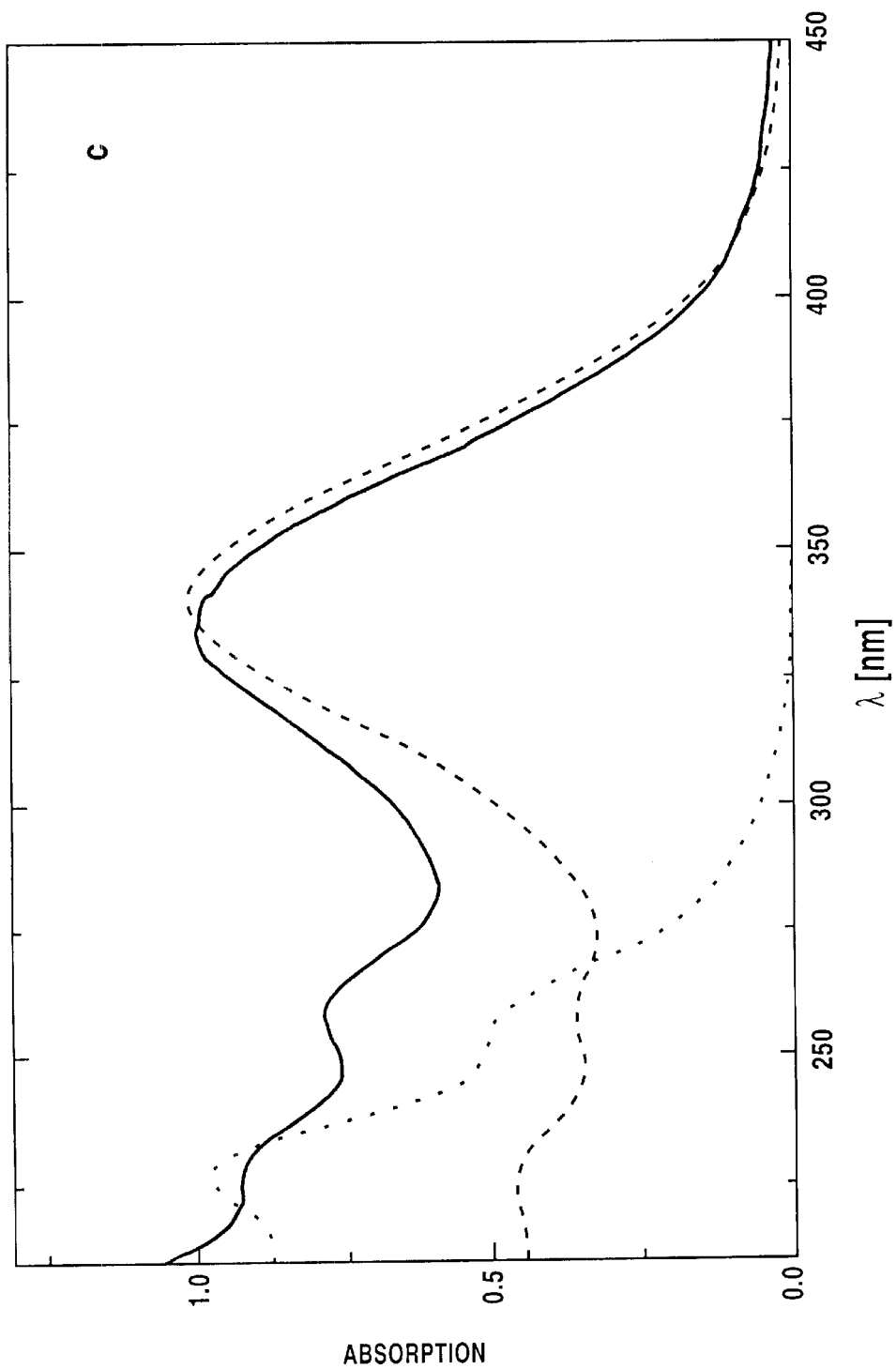

The spectrum of PM4VP retinoate films has more structure: Three maxima were found (FIG. 10c). The additional absorption bands are attributable to the UV activity of the quaternary vinylpyridinium unit. In contrast to the spectra for the two other complexes, there is a prominent maximum at higher wavelength (334 nm). The spectrum shows a second maximum at 262 nm with a shoulder on the higher wavelength side and a third maximum at 226 nm. The low intensity of the higher-energy absorption in the range from 250 to 270 nm for PM4VP retinoate compared with the absorption at short wavelengths of the other two complexes is attributed to the great effect of the N-methyl-pyridinium chromophore on the retinoate. The same spectra are observed after redissolving and after subsequent recasting as film. The data are summarized in Table 1.

TABLE 1

|  | $\lambda_{max.1}$ [nm] | $\lambda_{max.2}$ [nm] | $\lambda_{max.3}$ [nm] |
|---|---|---|---|
| Retinoic acid methanolic solution | 348 | | |
| PDADMAC retinoate (solution) | 336 | | |
| PDADMAC retinoate (film) | 319 | 252 | |
| Polyionene-6,3 retinoate (solution) | 337 | | |
| Polyionene-6,3 retinoate (film) | 297 | 253 | |
| PM4VP solution | | 257 | 226 |
| PM4VP retinoate (solution) | 340 | 257 | 226 |
| PM4VP retinoate (film) | 334 | 262 | 226 |

EXAMPLE 6

Preparation of Complexes of Vitamin A Acid with Cationic Polyamino Acids

Polyamino acids are polyelectrolytes which, in contrast to other polyelectrolytes which can be used according to the invention, are readily biodegradable. This may be particularly advantageous for various areas of application. The preparation of preferred poly-L-amino acid retinoate complexes is described below. The preparation of polyethyleneimine retinoate complexes can be carried out correspondingly.

6.1 Poly-L-lysine Retinoate 50 mg (0.24 mmol) of poly-L-lysine·HBr (Sigma/Aldrich) were dissolved in 20 ml of demineralized water and adjusted to pH 9 with 10% strength sodium hydroxide solution. Then 71.8 mg (0.24 mmol) of vitamin A acid (Fluka) were dissolved in 50 ml of demineralized water adjusted to pH 9 with sodium hydroxide solution. The solution of poly-L-lysine was then slowly added to the stirred vitamin A acid solution. A clear, pale yellow solution was produced and was stirred for a further one hour. This solution was then placed in an evaporating dish and left to stand, protected from the action of light, until the water had evaporated. A pale brown film was obtained. This film was crushed in a mortar and the resulting powder was washed several times with demineralized water to remove excess NaBr, and was then dried in air. Elemental analysis showed the following composition of the complex (in percent):

|  | $C_{26}H_{41}N_2O_3$ | | | | | |
|---|---|---|---|---|---|---|
| calculated | C 72.7 | H 9.5 | N 6.5 | O 11.2 | Na — | Br — |
| found | C 71.3 | H 9.7 | N 6.3 | O 12.7 | Na — | Br — |

These results prove a stoichiometric 1:1 complexation.

6.2 Poly-L-histidine Retinoate 78.4 mg (0.26 mmol) of vitamin A acid were dissolved in 50 ml of demineralized water which had been adjusted to pH 8 with sodium hydroxide solution. Then a solution of 100 mg (0.52 mmol) of poly-L-histidine·HCl was added, resulting in a fine, pale yellow precipitate. The precipitate was removed by centrifugation and washed several times with demineralized water. Elemental analysis showed the following composition of the complex (in percent):

|  | $C_{25}H_{36}N_3O_3$ | | | | | |
|---|---|---|---|---|---|---|
| calculated | C 71.2 | H 8.2 | N 9.6 | O 11.0 | Na — | Br — |
| found | C 70.4 | H 8.6 | N 9.7 | O 11.3 | Na — | Br — |

These results prove a stoichiometric 1:1 complexation.

6.3 Poly-L-arginine Retinoate

Solutions of 71.3 mg (0.24 mmol) of vitamin A acid in 50 ml of demineralized water and 50 mg (0.24 mmol) of poly-L-arginine·HCl (Sigma/Aldrich) in 20 ml of demineralized water were adjusted to pH 10 with sodium hydroxide solution. While stirring vigorously, the polyelectrolyte solution was added dropwise to the vitamin A acid. A pale yellow flocculant precipitate formed spontaneously. The solution was then stirred for about one hour, and the precipitate was subsequently removed by centrifugation. After washing several times with demineralized water, the resulting powder was dried in air. Elemental analysis showed the following composition of the complex (in percent):

|  | $C_{26}H_{41}N_4O_3$ | | | | | |
|---|---|---|---|---|---|---|
| calculated | C 68.2 | H 9.0 | N 12.2 | O 10.5 | Na — | Br — |
| found | C 68.4 | H 8.7 | N 12.7 | O 10.2 | Na — | Br — |

These results prove a stoichiometric 1:1 complexation.

EXAMPLE 7

Preparation of Nanodispersions of Vitamin A Acid Complexes

For intravenous administrations of drugs it is necessary, for example, for the pharmaceutical-containing particles in emulsions and dispersions to be sufficiently finely dispersed. The upper limit usually stated for the particle diameter is 5000 nm. It is shown below that the preparation of stable nanodispersions from vitamin A acid complexes according to the invention is possible in a straightforward manner. Nanodispersions according to the invention of all the complexes described in the examples can be obtained by the same process.

7.1 Preparation of a Nanodispersion

Equal amounts of a vitamin A acid complex according to the invention (20 mg of a poly-L-lysine retinoate) and of the dispersing aid Poloxamer 188 (20 mg) (ICI Surfactants, $(EO)_{76}$-co-$(PO)_{30}$, $M_w$=8350) were finely ground in a mortar. The resulting powder was then added in small portions, with vigorous stirring, to 15 ml portions of demineralized water, and the crude dispersion prepared in this way was treated with ultrasound 15 times for one minute each time. The dispersion should not be heated above 30° C. during this because, otherwise, there is a danger of a chemical decomposition of the vitamin A acid. Subsequently, the dispersion was purified through a filter (5 µm) in order to obtain the nanodispersion according to the invention.

7.2 Characterization of the Nanodispersions a. Particle Size Determination

The particle sizes in the nanodispersions according to the invention were obtained using the Nicomp submicron particle sizer, Model 370, Version 5.0. This apparatus uses the method of dynamic light scattering to measure the particle sizes in the range from 5 to 5000 nm.

TABLE 2

Intensity-weighted average particle diameters of the poly-L-amino acid retinoate complexes in the nanodispersions

| | Average particle diameter [nm] |
|---|---|
| Poly-L-lysine retinoate | 1422 |
| Poly-L-arginine retinoate | 378 |
| Poly-L-histidine retinoate | 362 |

The particle diameters showed no substantial changes when the nanodispersions were stored at 10° C. for a period of at least 3 months.

The particle sizes in the preferred embodiments are advantageously far below the limit of 5000 nm which is regarded as pharmacologically critical for intravenous administrations. The stability and particle sizes according to the invention mean that the nanodispersions according to the invention of the vitamin A acid complexes are very suitable for intravenous administrations.

b. Infrared Spectroscopy

To demonstrate intact complexes in the nanodispersions prepared, these underwent IR spectroscopic investigation (Impact 400 FT-IR apparatus, Nicolet Instrument Corp.).

As shown in Table 3, the typical carbonyl stretching band at 1690 cm-1 is absent for nanodispersions of poly-L-amino acid retinoate complexes. Instead of this there is found to be at least one other band at about 1645 cm-1, which is typical of complexed vitamin A acid. Thus there is no free vitamin A acid present in the nanodispersions according to the invention.

TABLE 3

Characteristic IR band positions for poly-L-amino acid retinoate complexes in nanodispersions

| Sample | 1st signal [cm$^{-1}$] | 2nd signal [cm$^{-1}$] | 3rd signal |
|---|---|---|---|
| Poly-L-lysine retinoate | 1645 | — | — |
| Poly-L-arginine retinoate | 1639 | 1662 | — |
| Poly-L-histidine retinoate | 1643 | 1661 | — |
| Vitamin A acid (in ethanol) | — | — | 1690 | c. UV Spectroscopy

To demonstrate the presence of intact complexes in the nanodispersions prepared, UV spectra (UVIKON 931, Kontron Instruments) were recorded (cf. Example 5, Table 1). The complexed vitamin A acid can be identified by the fact that the absorption band shows, compared with free vitamin A acid, a distinct hypsochromic shift (blue shift, shift to smaller wavelengths) and/or another band at lower wavelengths.

TABLE 3

UV absorption maxima for the poly-L-amino acid retinoate complexes in the nanodispersions

| Sample | 1st abs. band [nm] | 2nd abs. band [nm] |
|---|---|---|
| Poly-L-lysine retinoate | — | 289 |
| Poly-L-arginine retinoate | 334 | 286 |
| Poly-L-histidine retinoate | 330 | 289 |
| Vitamin A acid (in ethanol) | 348 | — |

What is claimed is:

1. A mesomorphic complex of vitamin A acid and cationic polyelectrolytes wherein said cationic polyelectrolytes are polyethyleneimine or a poly-L-amino acid.

2. A complex as claimed in claim 1, wherein the poly-L-amino acid is poly-L-arginine, poly-L-histidine, poly-L-lysine or a mixture thereof.

3. A complex as claimed in claim 1, which comprises up to 70% (w/w) vitamin A acid.

4. A complex as claimed in claim 1, wherein the vitamin A acid and the cationic polyelectrolyte are present in a stoichiometric ratio of 1:1.

5. A complex as claimed in claim 1, which is in the form of a viscoelastic film.

6. A complex as claimed in claim 1, which is present as particles in a nanodispersion together with a dispersing aid, the particle diameter being ≦5000 nm.

7. A complex as claimed in claim 6, wherein the dispersing aid is poloxamer 188.

8. A complex as claimed in claim 6, wherein the complex and the dispersing aid are present in stoichiometrically equal amounts.

9. A complex as claimed in claim 6, wherein the particle diameter is 200 to 5000 nm.

10. A process for preparing mesomorphic complexes of vitamin A acid and cationic polyelectrolytes, wherein said cationic polyelectrolytes are polyethyleneimine or a poly-L-amino acid, which comprises mixing solutions of vitamin A acid and of a cationic polyelectrolyte, isolating the mesomorphic complexes which have formed and optionally, purifying the complexes.

11. process as claimed in claim 10, wherein polyethyleneimine or poly-L-amino acids are used as polyelectrolytes.

12. A process as claimed in claim 11, wherein poly-L-arginine, poly-L-histidine, poly-L-lysine or a mixture thereof is used as poly-L-amino acid.

13. A process as claimed in claim 10, wherein a basic solution is used.

14. A method of using the mesomorphic complexes of claim 1 as a vitamin A substitute comprising applying the mesomorphic complexes to a subject's skin.

15. The method of use as claimed in claim 14, wherein the complexes are employed for treating skin disorders or for inhibiting the growth of malignant tumors.

16. A pharmaceutical composition which comprises at least one mesomorphic complex as claimed in claim 1.

17. A complex as claimed in claim 6, wherein the particle diameter is 250 to 3000 nm.

18. A complex as claimed in claim 6, wherein the particle diameter is 300 to 2000 nm.

19. A complex as claimed in claim 6, wherein the particle diameter is 350 to 1500 nm.

* * * * *